United States Patent [19]

Nürnberg et al.

[11] Patent Number: 5,288,501
[45] Date of Patent: Feb. 22, 1994

[54] MECHANICALLY-STABLE, READILY-DISINTEGRATABLE TABLETS MADE OF SMALL PREFORMED PARTICLES CONTAINING ACTIVE INGREDIENTS

[75] Inventors: Eberhard Nürnberg, Uttenreuth/Weiher; Erhard Seiller, Nidderau; Bernd Kühn, Frankfurt, all of Fed. Rep. of Germany

[73] Assignee: Merz + Co. GmbH & Co., Frankfurt, Fed. Rep. of Germany

[21] Appl. No.: 905,036

[22] Filed: Jun. 26, 1992

[30] Foreign Application Priority Data

Jul. 4, 1991 [DE] Fed. Rep. of Germany ....... 4122217

[51] Int. Cl.⁵ .............................................. A61K 9/20
[52] U.S. Cl. .................................... 424/465; 424/499; 424/480; 424/482; 514/781; 514/772.2
[58] Field of Search .............................. 514/772.2, 781; 424/499, 465, 480, 482

[56] References Cited

U.S. PATENT DOCUMENTS

| | | | |
|---|---|---|---|
| Re. 33,670 | 8/1991 | Maglio | 514/772.2 |
| 2,691,619 | 10/1954 | Bavley et al. | 424/499 |
| 2,805,977 | 9/1957 | Robinson et al. | 424/499 |
| 4,110,431 | 8/1978 | Oita | 514/781 |
| 4,159,345 | 6/1979 | Takev et al. | 424/362 |
| 4,460,562 | 7/1984 | Keith et al. | 514/772.2 |

FOREIGN PATENT DOCUMENTS

| | | | |
|---|---|---|---|
| 58-038211 | 3/1983 | Japan | 514/772.2 |
| 65-150628 | 5/1985 | Japan | 514/772.2 |

*Primary Examiner*—Paul R. Michl
*Assistant Examiner*—Peter F. Kulkosky
*Attorney, Agent, or Firm*—Gordon W. Hueschen

[57] ABSTRACT

The application discloses a process for the manufacture of mechanically-stable, readily-disintegratable tablets made of small preformed, preferably rounded, particles or pellets containing a high percentage of active ingredient in which—prior to compression—the particles are coated with an aqueous or aqueous/organic suspension containing water-soluble polyvinyl alcohol having an ester content of 19.4 to 6.7%, a disintegrant, and finely-divided cellulose, the remainder being excipients such as additional colloids, adjuvants, dyes, and/or flavors and the suspending liquid, and dried, the stable but readily-friable tablet product thus-produced, and a method of delivering an active ingredient by the employment of such a tablet for oral ingestion.

23 Claims, No Drawings

MECHANICALLY-STABLE, READILY-DISINTEGRATABLE TABLETS MADE OF SMALL PREFORMED PARTICLES CONTAINING ACTIVE INGREDIENTS

FIELD OF INVENTION

The invention relates to a process for the manufacture of tablets which comprise small preformed particles or pellets containing active ingredients, tablets so prepared, and a method of active ingredient delivery employing such tablets.

BACKGROUND OF INVENTION AND PRIOR ART

Various methods have been described for the manufacture of pharmaceutical compositions which continuously release the pharmaceutical ingredients over an extended period of time. One such method is to prepare a mixture of the active ingredient and a suitable, physiologically-acceptable vehicle such as, for example, a water-insoluble colloid with which water-soluble or water-swellable colloids may be admixed, and to extrude the admixture in strands of 0.5 to 3 mm in diameter, dividing these strands into 1 to 3 mm-long cylindrical particles. A second method is to soak or coat a physiologically-suitable vehicle in the form of pellets or particles with the active ingredient.

It has however been found that, when compressing such pharmaceutical-containing particles or pellets into tablets, unexpected difficulties arise. When compressed at a relatively low pressure, the tablets, when exposed to liquid, readily disintegrate into the individual components thereof, but exhibit only low mechanical stability and abrasion resistance, which may result in damage during further preparation for market, such as during filling into blister packs or transportation in other containers. On the contrary, when higher pressures are employed during the compression process, mechanically-stable tablets are obtained which exhibit considerably-retarded disintegration characteristics, so that the pharmacokinetic properties of the tablets differ substantially from those of the individual particles.

OBJECTS OF THE INVENTION

It is an object of the present invention to provide an improved process for the manufacture of tablets which have sufficient abrasion resistance but also adequate friability so as not to affect the release properties of active ingredients contained in individual particles or pellets comprised therein upon exposure to liquids and especially upon oral ingestion. A further object is the provision of tablets comprising small preformed particles or pellets containing active ingredients, preferably rounded, and which tablets exhibit improved characteristics as just stated. Another object of the invention is a method of delivering active ingredient contained in small preformed particles or pellets comprised in tablets according to the invention. Other objects of the invention will become apparent hereinafter and still others will be obvious to one skilled in the art to which this invention pertains.

SUMMARY OF THE INVENTION

The invention, then, comprises the following, inter alia, singly or in combination:

A process for the manufacture of mechanically-stable, readily-disintegratable tablets comprising small preformed individual pellets or particles containing active ingredient wherein A. an aqueous or aqueous-organic suspension which consists essentially of:
  a) water-soluble polyvinyl alcohol having an ester content between 19.4 and 6.7%,
  b) pharmaceutically-acceptable disintegrant,
  c) finely-divided cellulose, and
  d) pharmaceutically-acceptable excipients, the percentage by weight of said suspension of a) being 1–20, the percentage by weight of said suspension of b) being 1–20, the percentage by weight of said suspension of c) being 1–20, and the percentage by weight of said suspension of d) being 0 to 37%, the percentage by weight of a), b), c), and d) to total weight of the suspension being 3 to 40 percent, the remainder being the suspending liquid, is applied to the particles or pellets, whereafter B. the coated particles or pellets are dried, and C. the dried coated particles or pellets are compressed into tablets wherein the weight of the coating is at least 3% of the weight of the coated particles or pellets; such a process wherein the individual particles or pellets are rounded cylindrical pellets or particles; such a process wherein the disintegrant is cross-linked polyvinylpyrrolidone and the cellulose is in the form of cellulose powder or microcrystalline cellulose; such a process wherein the total amount of a), b), c), and d) in the suspension is about 15 to 25% by weight; such a process wherein the amounts of a), b), and c) in the suspension are each about 4 to 7% of the total weight of the suspension; such a process wherein the suspension contains about 4 to 7% by weight of a), about 4 to 7% by weight of b), and about 4 to 7% by weight of c), and the total amount of a), b), c), and d) in the suspension is about 15 to 25% by weight; such a process wherein the weight of the coating is about 5 to 60% of the weight of the coated particles or pellets; such a process wherein the weight of the coating is at least 10% of the weight of the coated particles or pellets; such a process wherein the dried particles or pellets are compressed into tablets on an excentric or rotary press, applying a pressure of 2 to 20 kN; such a process wherein the dried particles or pellets are compressed into tablets on an excentric or rotary press, applying a pressure between about 2 and 10 kN; such a process wherein the pressure applied is between about 2.5 and 5 kN; such a process wherein the excipient d) comprises a material selected from slightly-soluble polymethylmethacrylate, polyethyleneglycol, polyoxyethyleneglycol, and mixtures thereof; such a process wherein the excipient d) comprises a gastroresistant, film-forming substance selected from the group consisting of anionic polymethacrylate, cellulose acetate phthalate, and hydroxypropylmethylcellulose phthalate; such a process wherein the excipient d) comprises a slightly-soluble polymer selected from the group consisting of ethylcellulose, cellulose acetate, polyvinyl acetate, and a polymethacrylate having cationic ammonium groups; such a process wherein the tablets are coated with a film-forming substance containing at least one additional ingredient selected from the group consisting of a pigment, sugar, other sweetener, dye, flavor, lubricant, and softener; and any such process wherein the disintegrant b) is cross-linked polyvinylpyrrolidone and the cellulose c) is cellulose powder or microcrystalline cellulose.

Also, a mechanically-stable, readily-disintegratable tablet comprising small preformed particles or pellets containing active ingredient surrounded by an aqueous or aqueous-organic suspension which consists essentially of a) water-soluble polyvinyl alcohol having an ester content between 19.4 and 6.7%,
b) pharmaceutically-acceptable disintegrant,
c) finely-divided cellulose, and
d) pharmaceutically-acceptable excipients, the percentage by weight of said suspension of a) being 1-20, the percentage by weight of said suspension of b) being 1-20, the percentage by weight of said suspension of c) being 1-20, and the percentage by weight of said suspension of d) being 0 to 37%, the percentage by weight of a), b), c), and d) to total weight of the suspension being 3 to 40 percent, the remainder being the suspending liquid, the coated particles or pellets, after drying, having been compressed into a tablet under a pressure of 2-20 N, said tablet being abrasion resistant but rapidly disintegratable in water within a period of 5 to 300 seconds, said tablet having a hardness of between about 25 and 125 kN, and such a tablet wherein the suspension contains about 4 to 7% by weight of a), about 4 to 7% by weight of b), and about 4 to 7% by weight of c), and the total amount of a), b), c), and d) in the suspension is about 15 to 25% by weight, wherein the weight of the coating is about 5 to 60% of the weight of the coated particles or pellets, wherein the disintegrant b) is cross-linked polyvinylpyrrolidone and the cellulose c) is cellulose powder or microcrystalline cellulose, compressed into tablet form under a pressure between about 2 and 10 kN and having a disintegration time in water between about 15 and 60 seconds, and having a hardness between about 40 and 80 N.

Moreover, a method of delivering an active ingredient to a patient in need thereof, comprising the step of orally administering such a tablet to the said patient.

THE INVENTION

The subject matter of the present invention is a process for the manufacture of tablets comprising drug-containing small particles or pellets which rapidly disintegrate into the individual particles or pellets. The aim of this project was to prepare a tablet with sufficient abrasion resistance so as to be mechanically-stable but with sufficient friability so as not to affect the release properties of the active ingredients from the individual particles themselves upon oral ingestion. Unexpectedly, it was found that the problem can be solved by coating the small active-ingredient-containing particles or pellets with the following components:

water-soluble polyvinyl alcohol having an ester content (polyvinyl acetate) of 19.4 to 6.7%, a disintegrant, and finely-divided cellulose, with additional colloids, adjuvants, dyes and/or flavors, as required or desired, being optional.

The individual drug-containing particles or pellets are small preformed particles or pellets usually having a size not greater than about 3 mm on their largest dimension and are preferably rounded and between about 0.2 and 3 mm on their largest dimension, most preferably between about 0.4 and 0.2 mm, especially 0.5-1.5 mm on their largest dimension.

Such particles or pellets are coated with the foregoing-identified components according to known procedure in the form of an aqueous or aqueous/organic e.g., water-ethanol, suspension thereof containing 1 to 20, preferably about 4-7 percent by weight of the polyvinyl alcohol; 1 to 20, preferable 4-7 percent by weight of disintegrant; 1 to 20, preferably 4-7 percent by weight of finely-divided cellulose; and 0-37% of excipients selected from 0-20 percent by weight of one or more additional colloids and/or other adjuvants or auxilliary agents and 0-20 percent by weight of one or more excipients selected from flavors and/or dyes, the remainder being the suspending fluid or liquid present in the suspension, comprising, e.g., at least about 60 and preferably about 75 to 85 percent by weight thereof. The coating can be effected in several steps, for example, by spraying in a coating pan with intermediate drying phases, or by continuous spraying and subsequent drying. The temperature of the inlet air for drying is selected in accordance with the sensitivity of the active ingredient. The coating layer should be 3-60 percent by weight of the coated particles or pellets, preferably 5-60% of the weight of the coated pellets or particles, and most preferably at least about 10 percent by weight of the coated pellets or particles.

Subsequently, the coated and dried particles or pellets can be compressed into tablets containing the desired active ingredient on an excentric or rotary press. The pressure ranges employed are between 2 and 20 kN, preferably 2 to 10 kN, and especially 2.5-5 kN. The compressed tablets thus-prepared have sufficient breaking and abrasion resistance and rapidly disintegrate in water, i.e., within 5 to 300 seconds, preferably 15 to 60 seconds, into the original particles, and generally have a hardness between about 25 and 125 N, preferably between about 40 and 80 N. Accordingly, the pharmacokinetic properties of the tablets are, as desired, identical with those of the individual particles or of hard capsules filled with the same individual particles.

A salient characteristic of the process according to the invention is that the surface of the particle coatings is not completely smooth but rather relatively rough, as can be determined under an electron microscope. This roughness ensures good entanglement of the individual particles or pellets upon compression into tablets, even at lower pressures.

If desired, the thus-prepared compressed tablets can also be coated. Such coating may consist of or comprise any suitable pharmaceutically-acceptable film-forming substance, innumerable of which are known, e.g., hydroxypropylcellulose, hydroxypropylmethylcellulose, cellulose acetate phthalate, methylmethacrylate, or the like, if required or desired with addition of softeners, lubricants, and other adjuvants such as pigments, sugar or other sweetener, dyes, and/or flavors.

The disintegrant employed according to the invention is preferably cross-linked polyvinylpyrrolidone. The finely-divided cellulose is preferably employed in the form of cellulose powder and/or microcrystalline cellulose.

Any excipients employed may include additional colloids, which can preferably be a slightly-soluble polymethacrylate, PEG, or PEOG, or mixtures thereof, e.g., a Macrogol ™ such as, for example, Macrogol 6000 ™, the Macrogols being mixtures of polyethyleneglycols (PEGs) and polyoxyethyleneglycols (POEGs) of different molecular weights, the numerical designation being indicative of the molecular weight of both ingredients, e.g., 6000, with MWs of 4000 and above being preferred.

Additional pharmaceutically-acceptable excipients or adjuvants which may be used can be slightly-soluble polymers such as ethyl cellulose, cellulose acetate, or polyvinyl acetate having cationic ammonium groups, and/or gastro-resistant substances such as anionic polymethylmethacrylate, cellulose acetate phthalate, or hydroxypropylmethylcellulose phthalate.

The dyes and flavors to be employed are known to the art. The selection of such specific ingredients depends as usual on the desired result and is a part of the knowledge or one skilled in the art.

DETAILED DESCRIPTION OF THE INVENTION

The following examples are given by way of illustration only and are not to be construed as limiting.

EXAMPLE 1

A. Extrusion pellets are prepared according to the following formula:

| Ibuprofen | 67.2 g | 84% |
| --- | --- | --- |
| Polymethacrylate with cationic ammonium groups (Eudragit RS 30D ™), calculated as solid substance | 8.0 g | 10% |
| Triacetin | 0.8 g | 1% |
| Sodium carboxymethyl cellulose | 4.0 | 5% |
| Total moisture content | | 23% |

The moist mixture is extruded in a cylinder granulator, the cylindrical particles obtained being immediately rounded and dried.

B. Coating suspension

A suspension of the following components is prepared under vigorous stirring:

| Polyvinyl alcohol (Mowiol 4-88 ™) | 4.6% |
| --- | --- |
| Cross-linked polyvinylpyrrolidone (Crospovidone, Kollidon CL ™) | 7% |
| Cellulose powder (Vitacel M 80 K ™) | 6.8% |
| Macrogol 6000 ™ | 0.2% |
| Banana flavor | 1.4% |
| Water | 80% |
| | 100% |

C. Preparation of Coated Particles

Coat 680 g of the particles prepared according to Step A in a coating pan in several steps by spraying with a suspension according to B, the dried substance content of which is 120 g. Carefully dry the particles between the individual coating phases.

D. Tabletting

From the coated, well-dried particles according to C, tablets are compressed on an excentric or rotary press using a pressure of 3–3.5 kN. Each tablet contains 500 mg of active ingredient, corresponding to 700–750 mg of coated extrusion pellets.

Upon exposure to fluids, especially synthetic stomach fluids, or upon oral ingestion, it is found that the tablets of this example are particularly well suited to act as a delivery system for the delivery of active ingredient upon oral administration, since the tablet is characterized by sufficient abrasion resistance but also sufficient friability so as not to affect the release properties of the active ingredient from the individual particles themselves upon oral ingestion, thus providing rapid disintegration of the preformed tablet into the individual preformed active ingredient-containing particles or pellets.

EXAMPLE 2

A. Extrusion pellets are prepared according to the following formula:

| Paracetamol, fine crystals | 70% | 350 mg |
| --- | --- | --- |
| Avicel RC 581 ™ (microcrystalline cellulose) | 20% | 100 mg |
| Avicel CL 611 ™ | 10% | 50 g |
| Demineralized water plus | 35% | 173 g |

The moist powder mixture is processed on a cylinder granulator into cylindrical pellets having a diameter of 1.2 mm and a length of 3–4 mm. These pellets are finally rounded out in still wet condition and dried well.

B. Coating suspension

A suspension of the following components is prepared under vigorous stirring:

| Polyvinyl alcohol (Mowiol 3-83 ™) | 4.5% | 16.6 g |
| --- | --- | --- |
| Cross-linked polyvinylpyrrolidone (Polyplasdone XL ™) | 5.2% | 19.2 g |
| Cellulose powder (Elcema P 050 ™) | 5.1% | 18.9 g |
| Sodium cyclamate | 0.2% | 0.8 g |
| Demineralized water | 85.0% | 314.5 g |
| | 100% | |

C. Preparation of coated particles

Introduce 500 g of the pellets prepared according to A into a fluidized-bed apparatus (Aeromatic STREA 1 ™) and coat with the suspension prepared according to B, the dry solids content of which is 55.5 g (corresponding to a solids content of 15%). The percentage of the coating in relation to the total pellet material is about 10%. Subsequently, spray on Macrogol 6000 ™ from an aqueous solution to prepare a final coating of 0.5%, again related to the total pellet material.

The active ingredient content of the resulting coated pellets is about 63% by weight.

D. Tabletting

From the well-dried, coated particles prepared according to C, tablets are compressed on an excentric or rotary press using 9×15 mm pressing tools and a pressure of 3.0–4.0 kN. Each tablet contains 500 mg of active ingredient, corresponding to 750 to 800 mg of coated extrusion pellets.

Upon exposure to fluids, especially synthetic stomach fluids, or upon oral ingestion, it is found that the tablets of this example are particularly well suited to act as a delivery system for the delivery of active ingredient upon oral administration, since the tablet is characterized by sufficient abrasion resistance but also sufficient friability so as not to affect the release properties of the active ingredient from the individual particles themselves upon oral ingestion, thus providing rapid disintegration of the preformed tablet into the individual preformed active ingredient-containing particles or pellets.

EXAMPLE 3

A. Preparation of pellet cores containing active ingredients

Introduce 1000 g of non-pareils (diameter 0.7–0.9 mm) into a coating pan and heat to 50° C. using a dip pipe. Spray a solution of the following formulation onto the cores in the coating pan using a two-fluid nozzle:

| l-Ephedrine hydrochloride | 24% | 330 g |
|---|---|---|
| Demineralized water | 75% | 1045 g |
| | 100% | |

Spray on the solution intermittently with intensive intermittent drying phases. The active ingredient content of the resulting pellets is 25% by weight.

B. Coating suspension

Prepare a solution from the following components under vigorous stirring:

| Polyvinyl alcohol (Mowiol 4-88 TM) | 6.6% | 110.0 g |
|---|---|---|
| Cross-linked polyvinylpyrrolidone | 6.0% | 100.0 g |
| Microcrystalline cellulose (Avicel PH 101 TM) | 6.0% | 100.0 g |
| Lemon flavor | 0.98% | 16.3 g |
| Saccharine sodium | 0.40% | 6.7 g |
| Indigotine blue | 0.01% | 0.16 g |
| L-yellow | 0.01% | 0.16 g |
| Demineralized water | 80.0% | 1333.0 g |
| | 100% | |

C. Preparation of the coated pellets

Introduce 1330 g of substance-containing pellets prepared according to A into a fluidized-bed apparatus (Aeromatic STREA 1 TM with Wurster unit) and spray with suspension according to B having an ingredient content of 333.3 g (corresponding to a solid content of 20%). Avoid overwetting and spray intermittently, if required. Dry the pellets thoroughly and spray with a solution of 0.5% Macrogol 6000 TM, related to the total pellet material, in demineralized water.

The coated pellets obtained contain about 20% of active ingredient and 20% of coating in relation to their total weight.

D. Tabletting

The thoroughly-dried coated particles are compressed into tablets on an excentric or rotary press using 10 mm pressing tools and a pressure of 2.3 to 3.0 kN. Each tablet contains 50.0 mg of active ingredient corresponding to 250–300 mg of coated substance-containing non-pareils.

Upon exposure to fluids, especially synthetic stomach fluids, or upon oral ingestion, it is found that the tablets of this example are particularly well suited to act as a delivery system for the delivery of active ingredient upon oral administration, since the tablet is characterized by sufficient abrasion resistance but also sufficient friability so as not to affect the release properties of the active ingredient from the individual particles themselves upon oral ingestion, thus providing rapid disintegration of the preformed tablet into the individual preformed active ingredient-containing particles or pellets.

It is therefore seen that a novel process for the preparation of rapidly-disintegratable tablets comprising small preformed and preferably rounded active-ingredient-containing particles or pellets has been provided, as well as the tablets themselves, which tablets are characterized by sufficient abrasion resistance but also sufficient friability so as not to affect the release properties of the active ingredients from the individual particles themselves upon oral ingestion, and a method of delivering active ingredients upon oral ingestion by means of a tablet of the present invention and prepared according to the process of the present invention.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

We claim:

1. Process for the manufacture of mechanically-stable, readily-disintegratable tablets which are disintegratable in water within a period of 5 of 300 seconds comprising small preformed individual pellets or particles containing active ingredient wherein A. an aqueous or aqueous-organic suspension which consists essentially of:
   a) water-soluble polyvinyl alcohol having an ester content up to about 20%,
   b) pharmaceutically-acceptable disintegrant,
   c) finely-divided cellulose, and
   d) pharmaceutically-acceptable excipients,
the percentage by weight of said suspension of a) being 1–20, the percentage by weight of said suspension of b) being 1–20, the percentage by weight of said suspension of c) being 1–20, and the percentage by weight of said suspension of d) being 0 to 37%, the percentage by weight of a), b), c), and d) to total weight of the suspension being 3 to 40 percent, the remainder being the suspending liquid, is applied to the particles or pellets, whereafter B. the coated particles or pellets are dried, and C the dried coated particles or pellets are compressed under pressure of at least 2 kN into tablets of about 25–125 N hardness wherein the weight of the coating is at least 3% of the weight of the coated particles or pellets.

2. Process according to claim 1, wherein the individual particles or pellets are rounded cylindrical pellets or particles.

3. Process according to claim 1, wherein the disintegrant is cross-linked polyvinylpyrrolidone and the cellulose is in the form of cellulose powder or microcrystalline cellulose.

4. Process according to claim 1, wherein the total amount of a), b), c), and d) in the suspension is about 15 to 25% by weight.

5. Process according to claim 1, wherein the amounts of a), b), and c) in the suspension are each about 4 to 7% of the total weight of the suspension.

6. Process according to claim 1, wherein the suspension contains about 4 to 7% by weight of a), about 4 to 7% by weight of b), and about 4 to 7% by weight of c), and the total amount of a), b), c), and d) in the suspension is about 15 to 25% by weight.

7. Process according to claim 6, wherein the weight of the coating is about 5 to 60% of the weight of the coated particles or pellets.

8. Process according to claim 6, wherein the weight of the coating is at least 10% of the weight of the coated particles or pellets.

9. Process according to claim 1, wherein the dried particles or pellets are compressed into tablets on an excentric or rotary press, applying a pressure of 2 to 20 kN.

10. Process according to claim 6, wherein the dried particles or pellets are compressed into tablets on an excentric or rotary press, applying a pressure between about 2 and 10 kN.

11. Process according to claim 10, wherein the pressure applied is between about 2.5 and 5 kN.

12. Process according to claim 1, wherein the excipient d) comprises a material selected from slightly-soluble polymethylmethacrylate, polyethyleneglycol, polyoxyethyleneglycol, and mixtures thereof.

13. Process according to claim 1, wherein the excipient d) comprises a gastro-resistant, film-forming substance selected from the group consisting of anionic polymethacrylate, cellulose acetate phthalate, and hydroxypropylmethylcellulose phthalate.

14. Process according to claim 1, wherein the excipient d) comprises a slightly-soluble polymer selected from the group consisting of ethylcellulose, cellulose acetate, polyvinyl acetate, and a polymethacrylate having cationic ammonium groups.

15. Process according to claim 1, wherein the tablets are coated with a film-forming substance containing at least one additional ingredient selected from the group consisting of a pigment, sugar, other sweetener, dye, flavor, lubricant, and softener.

16. Process of claim 7 wherein the disintegrant b) is cross-linked polyvinylpyrrolidone and the cellulose c) is cellulose powder or microcrystalline cellulose.

17. A mechanically-stable, readily-disintegratable tablet comprising small preformed particles or pellets containing active ingredient surrounded by an aqueous or aqueous-organic suspension which consists essentially of
a) water-soluble polyvinyl alcohol having an ester content up to about 20%,
b) pharmaceutically-acceptable disintegrant,
c) finely-divided cellulose, and
d) pharmaceutically-acceptable excipients,
the percentage by weight of said suspension of a) being 1-20, the percentage by weight of said suspension of b) being 1-20, the percentage by weight of said suspension of c) being 1-20, and the percentage by weight of said suspension of d) being 0 to 37%, the percentage by weight of a), b), c), and d) to total weight of the suspension being 3 to 40 percent, the remainder being the suspending liquid, the coated particles or pellets, after drying, having been compressed into a tablet under a pressure of at least 2 kN, said tablet being abrasion resistant bu rapidly disintegratable in water within a period of 5 to 300 seconds, said tablet having a hardness of between about 25 and 125 N.

18. A tablet which is disintegratable in water within a period of 5 to 300 seconds of claim 17, wherein the suspension contains about 4 to 7% by weight of a), about 4 to 7% by weight of b), and about 4 to 7% by weight of c), and the total amount of a), b), c), and d) in the suspension is about 15 to 25% by weight, wherein the weight of the coating is about 5 to 60% of the weight of the coated particles or pellets, wherein the disintegrant b) is cross-linked polyvinylpyrrolidone and the cellulose c) is cellulose powder or microcrystalline cellulose, compressed into tablet form under a pressure between about 2 and 10 kN and having a disintegration time in water between about 15 and 60 seconds, and having a hardness between about 40 and 80 N.

19. A method of delivering an active ingredient to a patient in need thereof, comprising the step of orally administering a tablet of claim 17 to the said patient.

20. A method of delivering an active ingredient to a patient in need thereof, comprising the step of orally administering a tablet of claim 18 to the said patient.

21. A tablet of claim 17, wherein the water-soluble polyvinyl alcohol has an ester content between about 19.4 and 6.7%.

22. A process of claim 1, wherein the water-soluble polyvinyl alcohol has an ester content between about 19.4 and 6.7%.

23. A tablet of claim 17, wherein the coated particles or pellets, after drying, have been compressed into a tablet under a pressure of 2-20 kN.

* * * * *

UNITED STATES PATENT AND TRADEMARK OFFICE
CERTIFICATE OF CORRECTION

PATENT NO. : 5,288,501
DATED : February 22, 1994
INVENTOR(S) : Eberhard Nürnberg, Erhard Seiller, and Bernd Kühn It is certified that error appears in the above-indentified patent and that said Letters Patent is hereby corrected as shown below:

Title Page, [56], right-hand column, line 6; "65-150628" should read -- 85-150628 --.
Col. 3, line 30; "N," at the beginning of the line should read -- kN, --.
Col. 3, line 33; "kN," should read -- N, --.
Col. 8, line 42; insert a period after "C".
Col. 9, line 38; after "tablet" insert -- which is disintegratable in water within a period of 5 to 300 seconds --.
Col. 10, line 12; "bu" at the end of the line should read -- but --.
Col. 10, lines 16 and 17; after "tablet" delete "which is disintegratable in water within a period of 5 to 300 seconds".

Signed and Sealed this

Twenty-third Day of August, 1994

Attest:

BRUCE LEHMAN

Attesting Officer

Commissioner of Patents and Trademarks